United States Patent [19]

Nikoonahad

[11] Patent Number: 4,852,575
[45] Date of Patent: Aug. 1, 1989

[54] ULTRASOUND FLOW MEASUREMENT APPARATUS

[75] Inventor: Mehrdad Nikoonahad, Peekskill, N.Y.

[73] Assignee: North American Philips Corporation, New York, N.Y.

[21] Appl. No.: 160,871

[22] Filed: Feb. 26, 1988

[51] Int. Cl.$^4$ .......................... A61B 8/06; G01P 5/00
[52] U.S. Cl. .......................... 128/660.01; 128/663.01; 73/861.25; 73/861.27
[58] Field of Search ................ 128/86, 663.01, 661.07, 128/662.01, 622.04; 73/642, 644, 606, 861.25, 861.27

[56] References Cited

U.S. PATENT DOCUMENTS

| | | |
|---|---|---|
| 4,183,249 | 1/1980 | Anderson .......................... 73/642 X |
| 4,566,333 | 1/1986 | Chubachi et al. ...................... 73/642 |
| 4,655,083 | 4/1987 | Chubachi ............................. 73/606 |

Primary Examiner—Francis Jaworski
Attorney, Agent, or Firm—Jack E. Haken

[57] ABSTRACT

An ultrasound lens is a solid rod with a front concave spherical surface which defines a back focal plane in the rod when the lens is immersed in a propagating medium. The opposite end of the rod has two flat rear surfaces which are attached to ultrasound transducers and are inclined with respect to the lens axis so that principal rays from each of the transducers propagate through the lens normal to the rear surface and intersect on the lens axis at the back focal plane.

Echo ultrasound signals obtained from a sample volume using the lens may be cross correlated to yield transverse flow measurement data in the sample volume.

5 Claims, 3 Drawing Sheets

ULTRASOUND FLOW MEASUREMENT APPARATUS

The invention relates to a lens for producing a plurality of closely spaced, focused beams of ultrasound energy. The lens is particularly useful in conjunction with apparatus for measuring transverse flow by cross correlation techniques.

BACKGROUND OF THE INVENTION

Echo ultrasound measurements based on doppler shift or time domain correlation of two successive A-lines can be used to measure a velocity component of a flowing fluid which is parallel to the ultrasound beam axis. These techniques are, however, relatively insensitive to transverse velocity components (that is, velocity components which are normal to the ultrasound beam axis). A cross correlation technique for measuring transverse flow velocity was described in Slurry Flow Velocity, Concentration and Particle size Measurement Using Flow Noise and Correlation Techniques, Ong and Beck, Measurement and Control, Vol. 8, 1975, pp. 453–461. However, this prior art system had very poor spatial resolution and, therefore, was unsuitable for flow imaging and for diagnostic blood flow measurement in living tissue.

SUMMARY OF THE INVENTION

The invention is an ultrasound lens which produces a plurality of very closely spaced focused beams of ultrasound energy which are useful, for example, in a cross correlation type transverse flow measurement system and in high spatial resolution flow imaging applications. The lens may also be advantageously used in differential phase contrast acoustic microscopy.

The lens comprises a body of solid material having a first end which is formed with a concave spherical depression. When the depression is immersed in a suitable ultrasound propagating medium, for example water, it functions as a converging ultrasound lens which has a back focal plane which is within the solid body and normal to a main axis thereof. The end of the body opposite the spherical lens is formed with at least two flat faces which are inclined with respect to the axis and are adapted for attachment of piezoelectric ultrasound transducers. The position of the transducers on the faces and the inclination angle thereof are selected so that the central rays of the transducers intersect on the axis at the back focal plane. After the rays traverse the lens, they travel parallel to the axis to two closely spaced nearby foci.

If the transducers are pulsed with a periodic train of electrical pulses, ultrasound pulses at the foci sample the flow periodically. Ultrasound echoes are reflected from scattering centers in a sample volume which surrounds the foci and are returned to the transducers where they produce echo signals which can be amplified and amplitude-detected. If detected echo signals are cross correlated, the location of the peak of the cross correlation function of the echo signals characterizes transverse flow in the sample volume.

In an alternate embodiment, the lens is constructed with three or more inclined rear faces. Cross correlation between transducers on the faces characterizes flow in two or more different transverse directions.

DESCRIPTION OF THE DRAWINGS

The invention may be understood by reference to the drawings in which.

DESCRIPTION OF A PREFERRED EMBODIMENT

Figure 1:
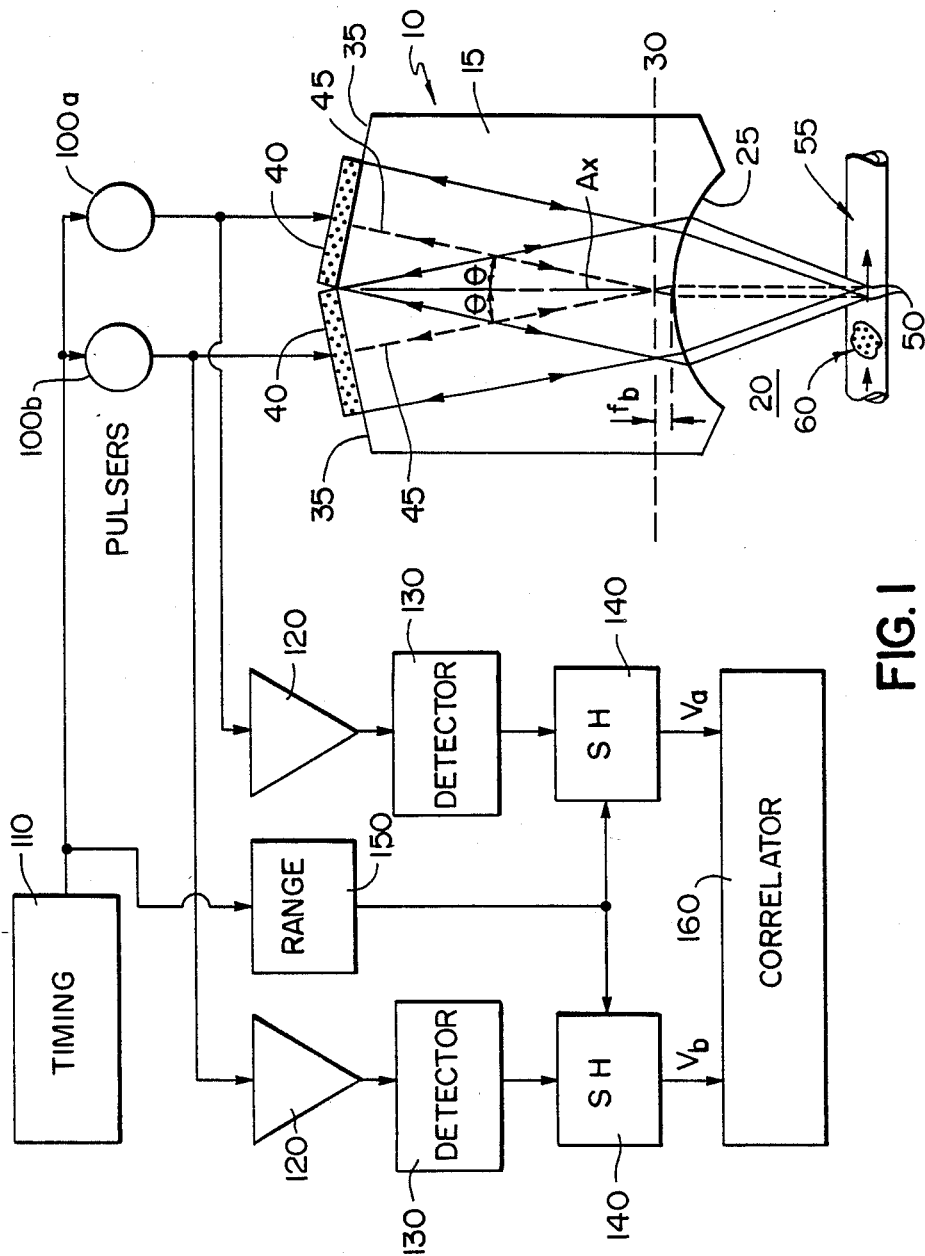
FIG. 1 illustrates the lens and flow measurement system.

An acoustic lens 10 is formed from a rod 15 of solid material which may, for example, be aluminum. A front surface of the rod has a concave spherical surface 25 and is immersed in an ultrasound propagating medium 20 which has a different ultrasound propagation velocity than the rod 15 and may, for example, be water. The concave surface 25 forms an acoustic lens having a back focal plane 30 which lies within the rod at a distance $f_b$ from the concave surface and is normal to a lens axis $A_x$ which extends along the rod. If the surface 25 has a radius R the focal plane distance $f_b = R/n - 1$ where n is the ratio of ultrasound propagation velocities across the surface 25.

The end of the rod opposite the concave surface 25 has two flat surfaces 35 which are inclined at equal angles with respect to the lens axis and are adapted for attachment of ultrasound transducers. Two transducers 40, which may for example be PZT ceramic wafers, are attached to the surfaces 35 so that principal rays 45 emitted by the transducers into the rod propagate at angles 8 with respect to the lens axis $A_x$ and intersect on the lens axis at the back focal plane 30.

After the principal rays 45 traverse the lens and exit through the curved surface 25 they propagate parallel to the lens axis to a pair of closely spaced front foci which are separated by a distance $\Delta x \delta 2 f_b$ tangent $\theta$.

The lens is arranged so that the foci lie in a sample volume which may contain a moving fluid, for example blood flowing through a vessel 55, which includes microscopic scattering centers 60. If the time taken for a volume of scatterers to travel the distance $\Delta x$ between the foci is t then the flow velocity is $v = \Delta x/t$.

A pair of ultrasound baseband pulsers 100a and 100b are connected to simultaneously excite the transducers 40 to produce periodic pulses of ultrasound energy under the control of a timing circuit 110. Energy from the transducers is reflected from the scattering centers at the respective foci in the moving fluid and returns to the respective transducers where it is converted into electrical signals which are amplified in amplifiers 120 and peak-detected in diode detectors 130. The outputs of the detectors are fed to two sample and hold circuits 140 under the control of a range gate 150, which is set to detect echoes from the sample volume at the foci 50, and are cross-correlated in a correlation stage 160. Alternately, the cross-correlation may be implemented in a general purpose digital computer.

If fluid is flowing through the sample volume, the output of the sample-and-hold circuits 140 constitutes two baseband signals $v_a$ and $v_b$ the frequencies of which depend on the rate at which scatterers intercept the foci. In an ideal case, where the scattering characteristics of the fluid do not change between the two foci 50, the output signals of the sample-and-hold circuits are identical but are shifted in time by t. In practice $v_a$ and $v_b$ are not quite identical and t must be measured using cross correlation algorithms.

In a practical embodiment, the lens 10 may comprise an aluminum rod in water (n=4.2), the lens radius R is 13 millimeters and the rear surface tilt angle $\theta$ is 14°. The back focal length of the lens is 4 millimeters and the front focal length 17 millimeters. The foci are separated by a distance $\Delta x$ of 2 millimeters. Alternately, the lens 10 may be constructed of quartz or another appropriate solid and/or the propagation medium may be tissue.

Figure 2:
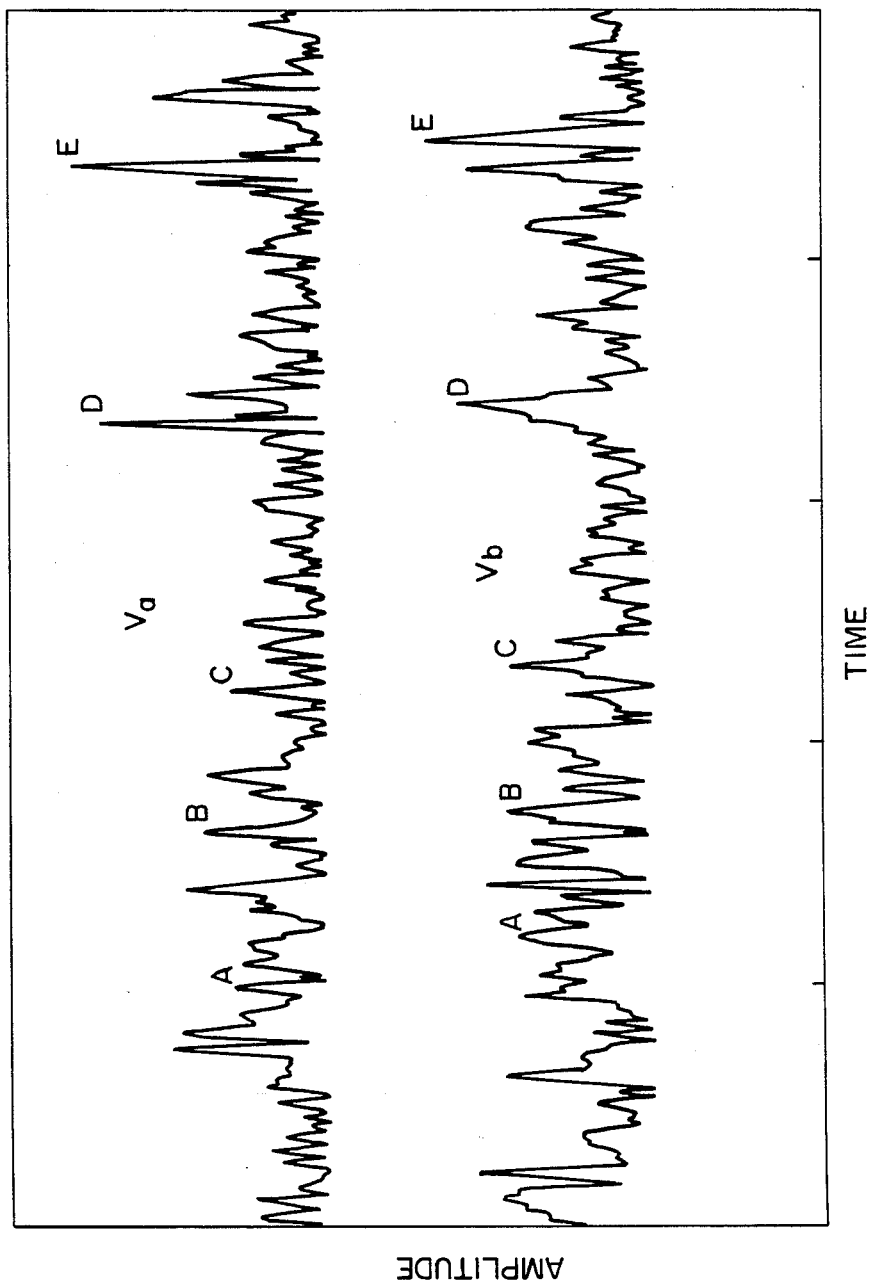
FIG. 2 illustrates echo signals from a flowing fluid in a sample volume.
Figure 3:
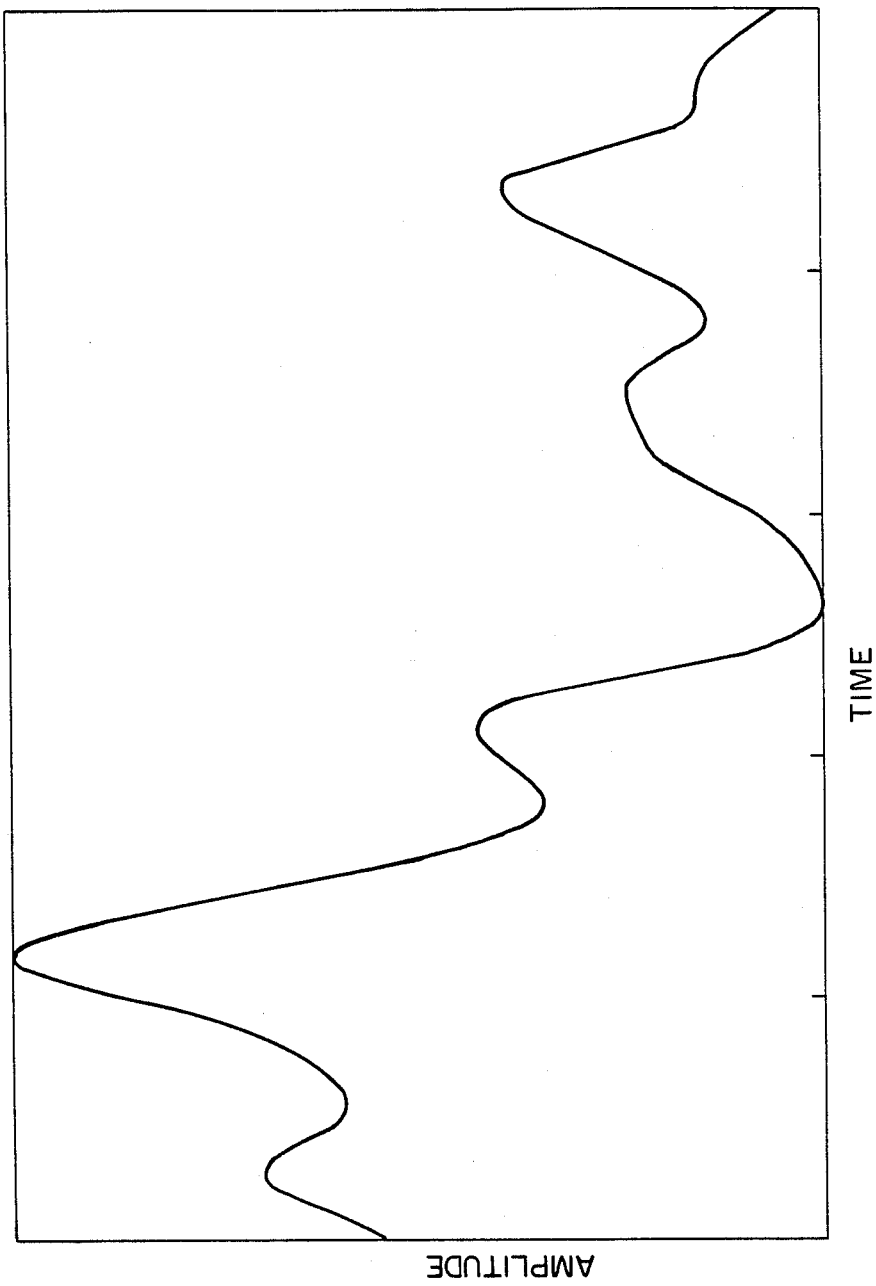
FIG. 3 illustrates the cross correlation of the signals in FIG. 2.

FIGS. 2 and 3 illustrates the signals $v_a$ and $v_b$ which were obtained from a measurement on the slurry of 600 micrometer alumina particles suspended in water flowing at a rate of 29 cc/s through a 6.4 millimeter diameter tube. Estimated flow velocity in the tube, assuming a uniform flow profile, was between 85 and 96 cm/sec. Each sample-and-hold circuit 140 had an output integration time of 1 millisecond. 1,000 samples of each signal were cross correlated in a digital computer based on 2,000 point fast Fourier transforms.

Recognizable features in the output waveforms $v_a$ and $v_b$ have been identified by identical letters in FIG. 2.

FIG. 3 shows the cross correlation of the two waveforms of FIG. 2. Under the experimental conditions set forth above, the correlation peak occurs at approximately 2.2 milliseconds which with $\Delta x = 2$ mm yields a transverse flow velocity at. of 91 cm/sec.

In an alternate embodiment, the rear end of the rod 15 may have three inclined surfaces with three attached transducers to produce three focused beams of ultrasound energy with foci in the sample volume. Signals from the three transducers may then be cross correlated to yield transverse flow velocity components in different directions which may be resolved into two orthogonal transverse velocity components.

What is claimed is:

1. Ultrasound flow measuring apparatus comprising:
   an ultrasound lens comprising a solid body having a front concave spherical surface which defines a back focal plane which lies within the body when the lens is in contact with a propagating medium and a lens axis which lies normal to said back focal plane, and at least two flat rear surfaces which are inclined at equal angles with respect to the lens axis, each of said rear surfaces being adapted for attachment of an ultrasound transducer so that principal rays of each of the transducers propagate through the body normal to the relevant rear surface and all of said principal rays intersect on the lens axis at the back focal plane;
   ultrasound transducers disposed on at least two of said rear surfaces;
   transmitter means connected to simultaneously excite each of the transducers with periodic pulses of baseband ultrasound energy whereby energy from said transducers is directed toward separate, nearby foci in a sample volume and echoes of said energy are reflected to said transducers;
   receiver means which amplify and amplitude detect signals representing the echoes reflected to the transducers from the sample volume; and
   means which cross correlate said detected signals from the transducers to characterize transverse flow in the sample volume.

2. The apparatus of claim 1 wherein two transducers are disposed on the rear surfaces.

3. The apparatus of claim 1 wherein three transducers are disposed on the rear surfaces to characterize flow in two different transverse directions.

4. The apparatus of claim 1 wherein the propagating medium is water.

5. The apparatus of claim 1 wherein the propagating medium is tissue.

* * * * *